United States Patent
Carr et al.

(10) Patent No.: US 6,232,496 B1
(45) Date of Patent: May 15, 2001

(54) PROCESS FOR THE PREPARATION OF AMPHOACETATE SURFACTANTS

(75) Inventors: John F. Carr, Morley; Peter Lees, Birkenshaw; Richard Stocks-Wilson, Hardwicke; Derek Pakenham, Headingley, all of (GB)

(73) Assignee: Rhone-Poulenc Chemicals Limited, Hertfordshire (GB)

( * ) Notice: Subject to any disclaimer, the term of this patent is extended or adjusted under 35 U.S.C. 154(b) by 0 days.

(21) Appl. No.: 08/561,057

(22) Filed: Nov. 22, 1995

(30) Foreign Application Priority Data

Nov. 22, 1994 (GB) .................................................. 9423573

(51) Int. Cl.⁷ ..................... C07C 231/12; B01F 17/22; B01F 17/24; C11D 1/88
(52) U.S. Cl. ........................... 562/564; 516/203; 562/565; 548/300.1; 548/352.1
(58) Field of Search ............................... 548/300.1, 352.1; 562/561, 564, 565; 252/356, 357; 516/203

(56) References Cited

U.S. PATENT DOCUMENTS

| | | | |
|---|---|---|---|
| 2,407,645 | * 9/1946 | Bersworth | 562/565 |
| 2,528,378 | * 10/1950 | Mannheimer | 548/352.1 |
| 2,773,068 | * 12/1956 | Mannheimer | 548/352.1 |
| 4,117,231 | * 9/1978 | Christiansen | 548/352.1 |
| 4,269,730 | * 5/1981 | Wechsler et al. | 252/356 |
| 4,705,893 | * 11/1987 | Sotoya et al. | 562/564 |
| 5,284,972 | * 2/1994 | Parker et al. | 562/565 |

* cited by examiner

Primary Examiner—Richard D. Lovering
Assistant Examiner—Daniel Metzmaier
(74) Attorney, Agent, or Firm—Burns, Doane, Swecker & Mathis, L.L.P.

(57) ABSTRACT

Amphoacetate surfactants are made by reacting a compound of formula $$RCONHCH_2CH_2NHCH_2CH_2OH$$

where R is an aliphatic radical, with formaldehyde and a cyanide of formula:

$R^1CN$, wherein $R^1$ represents a hydrogen atom or an alkali metal, and, when $R^1$ represents a hydrogen atom, hydrolysing the nitrile obtained with an alkali.

6 Claims, No Drawings

PROCESS FOR THE PREPARATION OF AMPHOACETATE SURFACTANTS

This invention relates to the preparation of amphocetate surfactants.

Amphoacetate surfactants, e.g. those sold under the registered Trade Mark "Miranol", are customarily made by reacting long chain fatty acids, e.g. in the form of the mixture known as "coconut fatty acids", with aminoethylethanolamine (AEEA), and reacting the product with a haloacetic acid or salt thereof in the presence of an alkali (see, for example, Kirk-Othmer's Encyclopedia of Chemical Technology Third Edition (Wiley & Sons) Vol. 22, pages 385 and 386 and U.S. Pat. Nos. 2,528,378 or 2,773,068). These reactions may be represented as follows:

$$RCOOH + H_2NCH_2CH_2NHCH_2CH_2OH \rightarrow$$
$$RCONHCH_2CH_2NHCH_2CH_2OH \quad (I)$$

and/or $$HOCH_2CH_2N(COR)CH_2CH_2NH_2 \quad (II)$$

where RCOOH is the long chain fatty acid. The diamide:

$$RCONHCH_2CH_2N(CH_2CH_2OH)COR \quad (III)$$

is formed as a by-product.

Both of products I and II may then undergo ring-closure with formation of an imidazoline of formula:

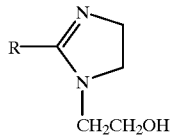

(IV)

It is preferably to convert this product into the open chain compound of formula I before (or simultaneously with) the reaction with the haloacetic acid in the presence of alkali, e.g. sodium hydroxide, which proceeds as follows:

$$RCONHCH_2CH_2NHCH_2CH_2OH + HalCH_2COOH \longrightarrow$$
(I)

$$RCONHCH_2CH_2NCH_2COOH$$
$$| $$
$$CH_2CH_2OH$$

(V)

The product of formula V, obtained in the form of a salt with the alkali used, is amphoteric and constitutes the desired amphoacetate surfactant.

Amphoacetate surfactants may function as anionic, cationic or nonionic surfactants, depending on the pH of the medium in which they are present. They are widely used in cosmetic formulations such as shampoos or cleansing detergents, because of their mildness, safety and lack of irritating effects on skin and eyes. They also have excellent surface active properties such as surface tension reduction, as measured for example by the pC-20 value (i.e. the amount needed to lower the surface activity by 20 units), and excellent foaming and wetting properties. They are compatible with both cationic and anionic surfactants. Because of their biodegradability, lack of skin irritation and unique ability to reduce the irritancy of more aggressive surfactants, such as ether sulfates, amphoacetate surfactants have gained wide use as secondary surfactants in the personal care industry. Furthermore, because of their hydrolytic stability and compatibility with electrolytes, they are also used in household and industrial cleaner formulations.

The haloacetic acid or salt thereof used in making such surfactants, generally sodium chloroacetate, may be involved in a number of side reactions, e.g.

1. Further reaction with amino functions of starting materials or products to produce polycarboxymethylated compounds;
2. Reaction with water to produce glycolic acid derivatives or with glycolic acid derivatives to produce diglycolates; and
3. Reaction with hydroxyethyl groups of starting materials or products to produce the corresponding carboxymethyl ethers.

Of these reactions, reactions of type 2 give rise to undesirable by-products (i.e. glycolates and/or diglycolates), which reduce the amount of haloacetic acid available for the desired reaction to produce the amphoacetate product.

We have found that commercially available coco/lauro amphoacetates contain as impurities (in addition to sodium chloride) the following major organic components:
- diamide of formula (III)
- Unalkylated amido-amine of formula (I)
- Glycolate/diglycolate
- sodium monochloracetate, and
- Sodium dichloroacetate The diamide is essentially inert (apart from a small amount of hydrolysis) to the reactions used to form the amphoacetate and so it is present in the product as an impurity. Its presence may be minimised by using an excess of AEEA in the first reaction. The presence of the diamide is undesirable because it causes poor long term stability with hazing and separation of the product.

The following Table shows the glycolic acid content obtained by analysing three commercial amphoacetates:

|  | GLYCOLIC ACID % |
| --- | --- |
| COMMERCIAL PRODUCT I | 2.6 |
| COMMERCIAL PRODUCT II | 2.4 |
| COMMERCIAL PRODUCT III | 2.0 |

This by-product glycolic acid is present as sodium glycolate. Its presence is undesirable because it does not contribute to the surface active properties of the product.

Sodium monochloroacetate and sodium dichloroacetate are both potential skin irritants and their presence is also undesirable.

The present invention provides a process for the preparation of an amphoacetate surfactant of significantly higher purity than that obtained by previously known methods. The new process comprises reacting a compound of formula $$RCONHCH_2CH_2NHCH_2CH_2OH \quad (I)$$

where R is a aliphatic radical of 5 to 19 carbon atoms, with formaldehyde and a cyanide of formula: $R^1CN$, wherein $R^1$ represents a hydrogen atom or an alkali metal, and, where $R^1$ represents a hydrogen atom, hydrolysing the nitrile obtained with an alkali.

This process may be represented (when hydrogen cyanide and an alkali metal hydroxide are used) as follows:

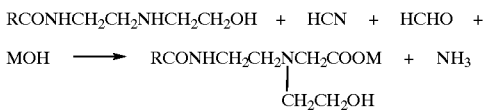

where R is as defined above and M represents an alkali metal, preferably sodium.

In one embodiment of the process, an alkali metal cyanide is used, normally in aqueous solution. In this embodiment the starting material of formula I may be reacted simultaneously with the formaldehyde and the alkali metal cyanide or first with the formaldehyde and then with the cyanide. The latter method has the advantage of minimising formation of nitrilotriacetic acid (NTA) impurity.

Alternatively, in either of these two methods, the cyanide compound used is hydrogen cyanide itself, and alkali is added subsequently.

The process of the invention is preferably carried out under atmospheric pressure to avoid excessive foaming of the product formed during the reaction. The use of atmospheric pressure, however, prevents the ammonia formed from boiling off. Accordingly, the reaction product is preferably subjected to a distillation step to remove excess water and ammonia. The excess ammonia may also optionally be removed by electrodialysis.

The alkali used in the process of the invention is preferably sodium hydroxide.

The molar ratio of the cyanide and the formaldehyde to the compound of formula I is at least 1:0:1.0 in each case, preferably from 1.2:1.0 to 1.0:1.0.

The starting materials of formula I generally contain mixtures of different R radicals within the range defined above. R is preferably a mixture of saturated and unsaturated aliphatic radicals derived from coconut oil or similar natural oil sources such as palm kernel oil or animal fat sources such as tallow. R is more preferably the residue of mixed coconut oil fatty acids, palm kernel oil fatty acids, a mixture of 70% $C_{12}$-alkyl and 30% $C_{14}$-alkyl fatty acids, or capric, caproic, caprylic, hexadecadienoic, lauric, linoleic, linolenic, margaric, myristic, myristoleic, oleic, palmitric, palmitoleic, or stearic acid, or a mixture thereof. More preferably R is derived from mixed coconut oil fatty acids with the following distribution by weight:

| | |
|---|---|
| C6 | ≦1 |
| C8 | 2–10 |
| C10 | 4–7 |
| C12 | 47–55 |
| C14 | 17–21 |
| C16 | 7–13 |
| C18 | 7–14 |
| >C18 | ≦0,5 |

The reaction is generally conducted at a temperature from about ambient temperature up to as high as about 100° C., preferably between 50° C. and 95° C. After the main reaction is considered complete, a higher temperature may be used to ensure completeness of reaction. The temperature during this portion of the reaction can range as high as 105° C. Suitable reaction times can be easily determined by a skilled artisan.

The product of the process of the invention contains substantially no alkali metal dichloroacetate or alkali metal monochloroacetate. It normally comprises less than 5% by weight, preferably less than 2% by weight, of alkali metal halide, less than 1% by weight of alkali metal glycolate and less than 0.5% of the diamide of formula (III). This unexpected reduction in the amount of diamide allows the possibility of lowering the AEEA: fatty acid radio used in the preparation of compounds of formula (I) and (II) thus reducing the amount of AEEA wasted.

The process of the invention thus gives a product having a high activity (expressed as % solids—(% alkali metal halide+% alkali metal glycolate)) and a low content of alkali metal dichloroacetate and alkali metal monochloroacetate which are potential skin irritants. The efficiency of the process is high and the starting materials are cheaper than in known processes.

The amphoacetate surfactants produced by the process of the present invention are extremely mild and non-irritating to both eyes and skin. On a by weight basis they exhibit enhanced wetting speed, greater surface tension reduction, and high foaming because of the higher activity. They also produce stable foams and have low toxicity and excellent compatibility with other anionic, ionic and nonionic surfactants. The products are stable over a wide pH range and are biodegradable. These properties make the surfactants useful in a wide range of products from cosmetics to industrial applications wherever amphoacetate surfactants have heretofore been in use. They are particularly useful for non-irritating shampoos, including baby shampoos, body shampoos, including bubble baths, bar soaps, bath gels, hair conditioning gels, lotions, skin creams, make-up removal creams and lotions, liquid detergents, dish detergents and other washing and cosmetic products that contact the skin. They are generally used in these applications at a concentration from 0.05 to 50%, preferably 0.5 to 10% by weight.

The amphoacetate surfactants produced by the process of the present invention may be used in preparations such as sprays, mousses, tonics, gels and lotions. The solvent or vehicle upon which these preparations are based depends upon the proposed use for the preparation. Suitable solvents include for example, water, lower alcohols, acetone, hydrocarbons (for example isobutane, hexane or decene), halogenated hydrocarbons (such as freons), esters (for example ethyl acetate or dibutylphthalate) and volatile silicones (in particular siloxanes such as phenyl pentamethyl siloxane or dimethicone) and their mixtures. When the preparations are in the form of sprays, lotions, tonics, gels or mousses, the preferred solvents include water, ethanol, volatile derivatives of silicone and their mixtures. These solvents when used as a mixture may be miscible or immiscible. Examples of gases to be used in mousses and aerosol sprays as the propellent gas include trichlorofluoromethane, dichlorodifluoromethane, difluoroethane, dimethylether, propane, n-butane or isobutane.

When the preparations comprise immiscible solvents, the preparations may be used in the form of an emulsion for example a water-in-oil, oil-in-water, or oil-in-water-in-silicone emulsion. These emulsions generally have a viscosity in the range from 100 to 200,000 cps. they may be delivered in the form of a spray using for example a disposable mechanical pump or in the form of an aerosol pressurized using a propellent gas.

These preparations comprising the surfactant prepared by the method of the invention generally also comprise additives such as fixing resins, protective polymers or stabilisers, plasticisers, and other surfactants. Other suitable additives include perfumes, colorants and/or opacifiers such as pigments eg. titanium dioxide particles. Bactericides or fungicides for example those which aid disinfection of skin (for example triclosan) may also be used. Further additives include humectants (for example glycerol, sorbitol, urea, collagen, gelatin or aloe vera), emulsifiers, powders or mineral particles (such as calcium carbonate or inorganic oxides in powder or colloidal form), preservatives (for example methyl, ethyl, propyl and butyl esters of hydroxybenzoic acid or sodium benzoate), osmotic agents, solar filters (particularly for use in compositions which protect skin or hair against damage from the sun or UV radiation), and thickening and gelling agents (such as polyacrylates, cellulose derivatives, or gums).

The surfactants prepared by the method of the invention may also be used in detergent compositions, particularly those used for washing by hand. Such compositions may be in liquid or powder form. These compositions generally comprise from 0.1 to 20% by weight, preferably from 0.5 to 10% by weight, of the surfactants prepared according to the method of the invention. The detergent compositions may also comprise other surfactants, builders, bleaching agents optionally in association with activators, anti-soil agents, anti-deposit agents, chelating agents, dispersants, brighteners, anti-foam agents, softeners, enzymes, alcohols, perfumes, pigments and buffering agents.

The surfactants prepared according to the invention may also be used as surface treatment agents for textiles (for lubrication, fire proofing, or softening) or for metals (for anti-corrosion or lubrication) and as anti-static agents for fibres and films of inorganic or organic polymers. They may equally be used for cleaning contact lenses or their accessories which are subject to prolonged contact with mucosal membranes and the surface of the eye.

The present invention is illustrated in the examples which follow.

EXAMPLE 1

Coconutamidoamine was prepared by the following method. 1201 g of molten imidazoline at approximately 70° C. was added to 1227 g of water in a 3-neck round bottomed flask. The self-emulsifying 2-phase mixture was stirred and 7 grams of 47% aqueous NaOH was added. The mixture was heated 80° C. and maintained at this temperature for 3 hours. It was then cooled to 45° C. when separation appeared from the homogeneous solution. The mass was made up with a few grams of water to 2435 g, discharged into a Winchester bottle and left to cool. Eventually the contents solidified as the product came out of solution.

Analysis:

Free-alkali=0.05% by weight NaOH

Equivalent weight=502.6 gmol$^{-1}$

The composition of the product was found on analysis to be as follows:

TABLE 1

| Analysis of Coconutamidoamine | % w/w |
|---|---|
| AMIDOAMINE of formula (I) | 42.0 |
| AMIDOAMINE of formula (II) | 4.2 |
| AEEA ($H_2NCH_2CH_2NHCH_2CH_2OH$) | 1.3 |
| DIAMIDE of formula (III) | 1.5 |
| IMIDAZOLINE | 0 |
| FATTY ACID (RCOOH) | 1.4 |
| FREE NaOH | 0.05 |

The starting imidazoline was prepared by the following method. 1620 kg of anhydrous aminoethylethanolamine (AEEA) was charged to the reaction vessel under vacuum and was then heated to 80° C. whilst being purged with nitrogen. 2280 kg of coconut fatty acid was metered in and heating was continued to a temperature of 150° C. The pressure was then reduced whilst further heating was applied to reach and maintain a temperature of 185° C. As the vacuum was applied, a water-based distillate was first collected, and thereafter an amine-based distillate was collected in a separate receiver down to a pressure of approximately 18 mbar. After the reaction was complete the batch was cooled to 65° C. and then discharged. No purification of the product was necessary.

EXAMPLE 2

The coconutamidoamine obtained in Example 1 was carboxymethylated by the following process.

A ten liter reaction flask was charged with 2,000 g of coconutamidoamine solution as prepared in Example 1, 1200 ml of water and 5 ml of 47% NaOH solution. NaCN solution and HCHO solution was metered over 46 minutes. The composition of the NaCN solution used was as follows:

250 g NaCN powder 575 ml water 6 ml 47% NaOH solution.

The HCHO solution was an aqueous solution containing 36% by weight of HCHO.

The reaction was carried out at atmosphere pressure and at a maximum temperature of 93° C. The temperature was mainly between 88 to 93° C. Foaming occurred and distillation was carried out after about 20 minutes of the addition period. After addition of the NaCN solution, its container and line were washed out into the reaction flask with 150 ml water. The free cyanide was reduced to about 32 ppm by addition of more HCHO solution. The total input of HCHO solution was 453 g. The reaction solution was distilled at atmospheric pressure for 4½ hours and the temperature raised to 101° C. There was much foam present but it was containable as long as the heating was not too vigorous. The reaction solution was concentrated to about 3 liters and on cooling a skin formed on the surface of the still hot liquor. 500 ml de-ionised water was added and a clear liquor was obtained on stirring. After filtration the liquor was diluted with de-ionised water to give a final weight of 3988 g (a volume of about 3725 ml). The solution obtained was a clear orange-brown solution.

1 kg of this solution was heated to 63° C. and 2 ml of 35% $H_2O_2$ was added. This was allowed to cool while being stirred and a yellow solution with a pH of 12.92 was obtained.

Full analysis of the sample (referred to below as A) gave the results given in Table 2 below. This table includes data analysis of a standard coconutamphoacetate (B) obtained by known prior art processes which use monochloroacetic acid and a coconutamphoacetate (C) obtained according to a similar process except that the pH was controlled to minimise production of unalkylated amide and glycolic acid.

TABLE 2

|  | B | C | A |
|---|---|---|---|
| SOLIDS % | 49.7 | 40.0 | 36.0 |
| SALT % | 11.6 | 7.0 | 1.4 |
| Na GLYCOLATE % | 6.3 | 1.5 | 0.2 |
| DIAMIDE % | 0.6 | 0.6 | 0.2 |
| AMIDO AMINE % | <0.1 | 0.5 | 0.4 |
| SMCA ppm | <50 | <20 | 0 |
| SDCA ppm | <200 | <50 | 0 |
| HEEDTA % | 0.8 | 0.5 | 1.8 |
| NTA % | 0 | 0 | 0.55 |
| $NH_3$ ppm | 0 | 0 | 140 |
| pH | 8.5 | 9.0 | 9.2 |
| ACTIVITY % | 31.8 | 31.5 | 34.4 |
| (SOLIDS-NaCl-Glycollate) | (64%) | (79%) | (95%) |
| ACTIVITY % | 30.3 | 29.9 | 31.0 |
| (SOLIDS - IMPURITIES) | (61%) | (75%) | (86%) | wherein SMCA is sodium monochloroacetate, SDCA is sodium dichloroacetate, HEEDTA is N-(2-hydroxyethyl) ethylenediaminetriacetic acid, and NTA is nitrilotriacetic acid.

EXAMPLE 3

In this example coconutamidoamine was reacted with formaldehyde to form the methylol derivative and then this derivative was reacted with sodium cyanide. The objective of this route was to reduce the content of nitrilotriacetic acid in the final product.

The coconutamidoamine was obtained by the process of Example 1 except that 1210 g of molten imidazoline, 1908 g of water and 7 g of 47% aqueous NaOH was used and heat was applied until the reaction mixture reached 80° C. and this temperature was then maintained for 4 hours. The solution was then analyzed:

Equivalent weight=465.7 g mol$^{-1}$.

From this value it was calculated that 153 g of paraformaldehyde was required for a 2.5% molar excess.

The solution was cooled to 60 to 65° C. and the paraformaldehyde was added gradually over approximately 1 hour. No evolution of heat was observed. After stirring at 65° C. for a further hour, the clear solution obtained was cooled. It was stable at room temperature without solidification.

Analysis:

Free-alkali=0.05% by weight NaOH

Equivalent weight=518 g mol$^{-1}$

The coconutamidoamine/paraformaldehyde reaction product was assumed to have the same active concentration as the coconutamidoamine obtained in Example 1.

The carboxymethylation reaction was carried out as follows.

A ten liter reaction flask was charged with 2,000 g of the coconutamidoamine/paraformaldehyde reaction product obtained above, 1200 ml water and 5 ml of 47% aqueous NaOH solution. A NaCN solution was metered in over 40 minutes. The composition of this solution was as follows:

208 g NaCN powder 485 ml water 5 ml of 47% aqueous NaOH solution the estimated mol ratio of NaCN: amine was 1:1. Distilling occurred after about 29 minutes of the addition period; only a small amount of foam was obtained. After the addition of the NaCN solution, its container and line was washed into the reaction flask with 150 ml water. After distilling at atmospheric pressure for 75 minutes, 500 ml of de-ionised ionised water was added. Distilling was continued for a further 70 minutes at a temperature of 101° C. Much foam was present. On cooling a skin formed on the surface of the still hot liquor. Its volume was about 3.25 liters. 400 ml of de-ionised water was added and on stirring a clear liquor was obtained. This liquor contained 1720 ppm of free cyanide. Distilling was continued at atmospheric pressure for 3 hours during which 500 ml de-ionised water was added. It was then allowed to stand overnight. A further 500 ml of de-ionised water was added to the flask. A further check on the liquor showed that it contained less than 56 ppm of free cyanide. The liquor was filtered and diluted with de-ionised water to a final weight of 4390 g. a clear orange-brown solution was obtained which was darker than the product from Example 2. One kilogram of this solution was heated to 64° C. and 4 ml of 35% $H_2O_2$ solution was added. This was allowed to cool while being stirred. A yellow solution was obtained which was more coloured than the equivalent solution in Example 2. Its pH was 12.61. The solution contained about 20 ppm of free cyanide.

The product was analysed and gave the following results.

TABLE 3

| PERCENTAGE SOLIDS | 32.0 |
| PERCENTAGE COCONUTAMIDOAMINE | 5.4 |
| PERCENTAGE NTA | <0.1 |

TABLE 3-continued

| FREE NaCN | approx 20 ppm |
| FREE CH$_2$O | 0 |
| pH | 12.6 |

The percentages are percentages by weight.

EXAMPLE 4

In this example, the carboxymethylation process according to Example 2 was investigated using a lower molar ratio of NaCN and CH$_2$O (the molar ratio used was 1.1:1). The coconutamidoamine solution used was prepared according to the method described in Example 1. The carboxymethylation process comprised charging a 10 liter reaction flask with 2000 g of the coconutamidoamine solution, 1200 ml water and 5 ml of 47% aqueous NaOH solution. NaCN solution and HCHO solution were metered over 41 minutes. The composition of the NaCN solution was as follows:

228 g NaCN powder 525 ml water 5.5 ml of 47% aqueous NaOH solution

The HCHO solution used was an aqueous solution containing 36% by weight of HCHO.

The reaction was carried out at atmospheric pressure and at a maximum temperature of 95° C. Foaming and distilling occurred after about 22 minutes of the addition period. The NaCH container and line were washed into the reaction flask with 150 ml water at the end of the addition period. The free cyanide level was reduced to about 80 ppm by the addition of HCHO solution. The total addition of the HCHO solution was 425 g. The resultant solution was distilled at atmospheric pressure for 4½ hours and the temperature raised to 100.5° C. Much foam was present but it was containable as long as heating was not too vigorous. The solution was concentrated to about 3.25 liters and on cooling a skin formed on the surface of the liquor. 250 ml of de-ionised water was added and on stirring a clear liquor was obtained.

A further 250 ml of de-ionised water was added and the solution was heated to 63° C. and 8 ml of 35% $H_2O_2$ was added. The mixture was allowed to cool while being stirred. The liquor was filtered and diluted with de-ionised water to a final weight of 398 g (a volume of about 3.75 liters). A yellow solution was obtained with a pH of 13.01. The pH of the solution was reduced to 9.4 (20%) by the addition of a small quantity of 36% hydrochloric acid. The analysis of the product was as follows:

TABLE 4

| Solids % | 35.7 |
| Salt % | 1.22 |
| Sodium Glycolate % | 0.15 |
| Diamide % | 0.2 |
| Amidoamine % | 0.3 |
| SMCA | 0 |
| SDCA | 0 |
| HEEDTA % | 1.4 |
| NTA % | <0.35 |
| NH$_3$ ppm | 114 |
| pH | 9.4 |
| Activity % (Solids-NaCl-Glycolate) | 34.33 (96%) |
| Activity % (Solids - Impurities) | 31.68 (89%) |

Thus the use of a lower molar ratio of sodium cyanide and formaldehyde has further reduced the impurity levels, including NTA. The activity/solids ratio is 96% which is far higher than that for a standard cocoamphoacetate.

EXAMPLE 5

The wetting power of the sample obtained in Example 2 (A) was compared with the product (C), using standard method NFT 73 40G or ISO 8022 using a pH of 6. In the test a cotton test disk is dropped into an aqueous solution of the wetting agent. The wetting power was determined by the concentration required for a sinking time of 100 seconds. Identical results were obtained for products A and C.

EXAMPLE 6

The foaming power of the sample obtained according to Example 2 (A) was compared with that of products (B) and (C) using standard method NF T 73 404 or ISO 696. for each surfactant the foam volume produced at a concentration of 1 g per liter in a medium with a pH of 6 was measured using distilled water, an aqueous solution of 0.0033 mol/l calcium and an aqueous solution of 0.1% sebum. Comparable results were obtained for products A, B and C.

EXAMPLE 7 the viscosity building power of the sample obtained according to Example 2 (A) was compared with the product (C). The composition of the blend used was as follows:

Sodium laurylethoxyethylsulphate 35%

Surfactant 6%

Water+NaCl to make up 100%

The pH was adjusted to 6 using citric acid. The following results were obtained:

TABLE 7

| | Relative Viscosity (mPa · s) | |
|---|---|---|
| % NaCl | A | C |
| 0 | 0 | 4 |
| 0.5 | 1 | 15 |
| 1 | 2 | 84 |
| 1.5 | 230 | 603 |
| 2 | 1880 | 3500 |
| 2.5 | 6630 | 8100 |

The dynamic viscosity was measured at 25° C. using a Brookfield viscosimeter, according to method AFNOR NFT 76 102, relative to the value for product A with 0% NaCl. The values for product C are greater than those for product A because product C has a larger residual amount of sodium chloride as a result of its preparation process as can be seen from Table 2 above. When this difference is taken into account the results obtained are comparable.

EXAMPLE 8

Laurylamidoamine was prepared according to the method of Example 1 using 25% by weight of lauryl imidazoline and a catalytic amount of sodium hydroxide. The product obtained contained in excess of 95% by weight of the linear amidoamine.

Formaldehyde was added to the product laurylamidoamine until a clear solution was obtained (1.2 molar equivalent of formaldehyde was used). Formaldehyde was used in the form of a 36% by weight solution of HCHO in water. The mixture was left overnight at room temperature.

The following morning 1.2 molar equivalents of liquid hydrogen cyanide were added in 30 minutes to the mixture heated to 45° C. The mixture obtained was then stirred at 45° C. for one hour.

The product was hydrolysed with 1.2 molar equivalents of sodium hydroxide at a temperature of 85° C. for four hours under a nitrogen atmosphere.

The analysis of the product obtained is given below in Table 8.

TABLE 8

| | analytical data |
|---|---|
| conversion amidoamine (% by weight) | 92 |
| chemical yield amphoacetate (% by weight) | 46 |
| cyanides (ppm) | 1840 |
| NTA (% by weight) | 0.25 |

The cyanide content was reduced to 260 ppm by treating the product with 1 molar equivalent of hydrogen peroxide at a temperature of 60° C. for four hours.

What is claimed is:

1. A process for the preparation of an amphoacetate surfactant, the process comprising reacting a compound of the formula (I):

$$RCONHCH_2CH_2NHCH_2CH_2OH \qquad (I)$$

where R is an aliphatic radical containing from 5 to 19 carbon atoms, with formaldehyde and a cyanide of formula $R^1CN$, wherein $R^1$ represents a hydrogen atom or an alkali metal, the molar ratio of the formaldehyde and the cyanide to the compound of formula (I) being at least 1.0:1.0, with the proviso that when $R^1$ represents a hydrogen atom, the nitrile obtained is hydrolyzed with an alkali.

2. A process according to claim 1, wherein R is derived from an acid selected from the group consisting of a coconut oil fatty acid, a palm kernel oil fatty acid, a mixture of $C_{12}$-alkyl and $C_{14}$-alkyl fatty acids, capric acid, caproic acid, caprylic acid, hexadecadieneoic acid, lauric acid, linoleic acid, linolenic acid, margaric acid, myristic acid, myristoleic acid, oleic acid, palmitic acid, palmitoleic acid, stearic acid, and a mixture thereof.

3. A process according to claim 1 wherein the alkali is sodium hydroxide.

4. A process according to claim 1 wherein from 1.0 to 1.2 moles of each of the cyanide and the formaldehyde is used.

5. A process according to claim 1 wherein the cyanide is an alkali metal cyanide.

6. A process according to claim 1 wherein the compound of formula (I) is obtained by hydrolysis of a corresponding imidazoline of formula (IV):

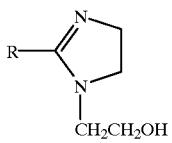

where R is as defined in claim 1.

* * * * *